(12) United States Patent
Haar et al.

(10) Patent No.: US 6,440,099 B2
(45) Date of Patent: Aug. 27, 2002

(54) HYPODERMIC NEEDLELESS INJECTION SYSTEM

(75) Inventors: Hans-Peter Haar, Wiesloch; Hans List, Hesseneck, both of (DE); George Bevan Kirby Meacham, Shaker Heights, OH (US)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/781,377

(22) Filed: Feb. 12, 2001

Related U.S. Application Data
(60) Provisional application No. 60/182,954, filed on Feb. 16, 2000.

(51) Int. Cl.$^7$ ................................................. A61M 5/30
(52) U.S. Cl. ......................................... 604/68; 604/70
(58) Field of Search ..................................... 604/68, 70

(56) References Cited

U.S. PATENT DOCUMENTS

| | | | |
|---|---|---|---|
| 2,680,439 A | | 6/1954 | Sutermeister |
| 3,625,208 A | * | 12/1971 | Frost et al. ................... 604/68 |
| 5,073,165 A | * | 12/1991 | Edwards ...................... 604/68 |

FOREIGN PATENT DOCUMENTS

| | | |
|---|---|---|
| GB | 993309 | 5/1965 |
| WO | 98/31409 | 7/1998 |

* cited by examiner

Primary Examiner—Philippe Derakshani
(74) Attorney, Agent, or Firm—George W. Johnston; Robert A. Silverman (57) ABSTRACT

A hypodermic needleless injection system for injecting a liquid medication, which system comprises: a medication unit configured and dimensioned to store a volume of liquid to be injected, the medication unit having a first region and a second region that are in liquid communication with each other, the first region being deformable and the second region having at least one orifice, a hydrostatic chamber containing a hydrostatic pressure transfer medium, the hydrostatic chamber being so configured and dimensioned that the medication unit is located at least partially within the hydrostatic chamber and so that a pressure exerted on the transfer medium would cause the first region of the medication unit to deform so as to reduce the volume available for the liquid medication within the medication unit, and a first piston having a first end and a second end opposite to the first end, the first end having a surface which forms a closure of the hydrostatic chamber, and is adapted for applying a pressure on the transfer medium contained in the hydrostatic chamber.

14 Claims, 5 Drawing Sheets

HYPODERMIC NEEDLELESS INJECTION SYSTEM

This application claims priority under 35 U.S.C. § 119(e) of provisional application(s) Ser. No. 60/182,954, filed Feb. 16, 2000.

FIELD OF THE INVENTION

The invention concerns a hypodermic needleless injection system for injecting a liquid medication.

BACKGROUND

International Patent Application with publication No. WO-A-98/31409 describes a hypodermic needleless injection system for injecting a liquid medication comprising a disposable medication cartridge and a reusable application device. The reusable application device includes a locking pressure chamber that contains and supports the cartridge, and other necessary subsystems including electric ignition and safety interlocks. The disposable cartridge contains a prefilled sterile single dose medication container and a small pyrotechnic gas generator that produces 200 to 300 bar pressure exerted on the medication container for carrying out the injection. The single dose medication container comprises a first region delimited by a thin walled, flexible plastic medication container and a second region having a jet nozzle. The gas pressure provided by the gas generator is applied on the thin walled container which collapses under that pressure and this causes ejection of the liquid through the jet nozzle.

In the known system disclosed by WO-A-98/31409 the thin wall of the medication chamber forms a barrier between the liquid medication and the high pressure gas. The latter thin wall is largely under hydrostatic pressure and carries only modest tensile and shear stresses. However in order to reduce the probability of gas contact with the liquid medication in the event of a single point failure of the thin flexible wall of the medication chamber, it is advisable to use a second wall, e.g. a rubber wall, which shields the thin wall of the medication chamber.

A disadvantage of the structure of the known system disclosed by WO-A-98/31409 is that it does not allow the use of low cost energy sources, e.g. mechanical devices or low pressure gas sources, for generating the necessary pressure on the deformable wall of the medication container.

This disadvantage thus raises the problem of how to modify the structure of the injection system in order that the modified structure allows the use of that low cost energy sources and allows thereby a reduction of the manufacture cost of the whole system.

SUMMARY OF THE INVENTION

The aim of the invention is therefore to provide a hypodermic needleless injection system for injecting a liquid medication which is adapted to make use of low cost energy sources and which thereby makes possible to reduce the manufacture cost of the injection system.

According to the invention this aim is attained with a hypodermic needleless injection system comprising:

(a) a medication unit configured and dimensioned to store a volume of liquid to be injected, said medication unit having a first region and a second region that are in liquid communication with each other, said first region being deformable and said second region having at least one orifice, (b) a hydrostatic chamber containing a hydrostatic pressure transfer medium, said hydrostatic chamber being so configured and dimensioned that the medication unit is located at least partially within the hydrostatic chamber and so that a pressure exerted on said transfer medium would cause said first region of said medication unit to deform so as to reduce the volume available for said liquid medication within said medication unit, and (c) a first piston having a first end and a second end opposite to said first end, said first end having a surface which is adapted for applying a pressure on said transfer medium contained in said hydrostatic chamber.

A preferred embodiment of a hypodermic needleless injection system according to the invention further comprises (d) an activatable force generator able to generate a force and to apply said force on said second end of said first piston in order to cause that said surface of said first end of piston applies a corresponding pressure on said transfer medium, and (e) and activation means for activating said force generator.

The main advantage of an injection system according to the invention is that it makes possible to attain the above mentioned aim. An additional advantage of a preferred embodiment of such a system is that it is apt to be manufactured entirely as a disposable injection system which can be provided to the user ready for use in a package which ensures sterility. In the context of the invention ready for use means prefilled with a predetermined amount of medication and without requiring any assembling step to be performed by the user before use.

BRIEF DESCRIPTION OF THE DRAWINGS

The subject invention will now be described in terms of its preferred embodiments. These embodiments are set forth to aid the understanding of the invention, but are not to be construed as limiting.

DETAILED DESCRIPTION OF THE INVENTION

Basic Structure of a Needleless Injection System According to the Invention

Figure 1:
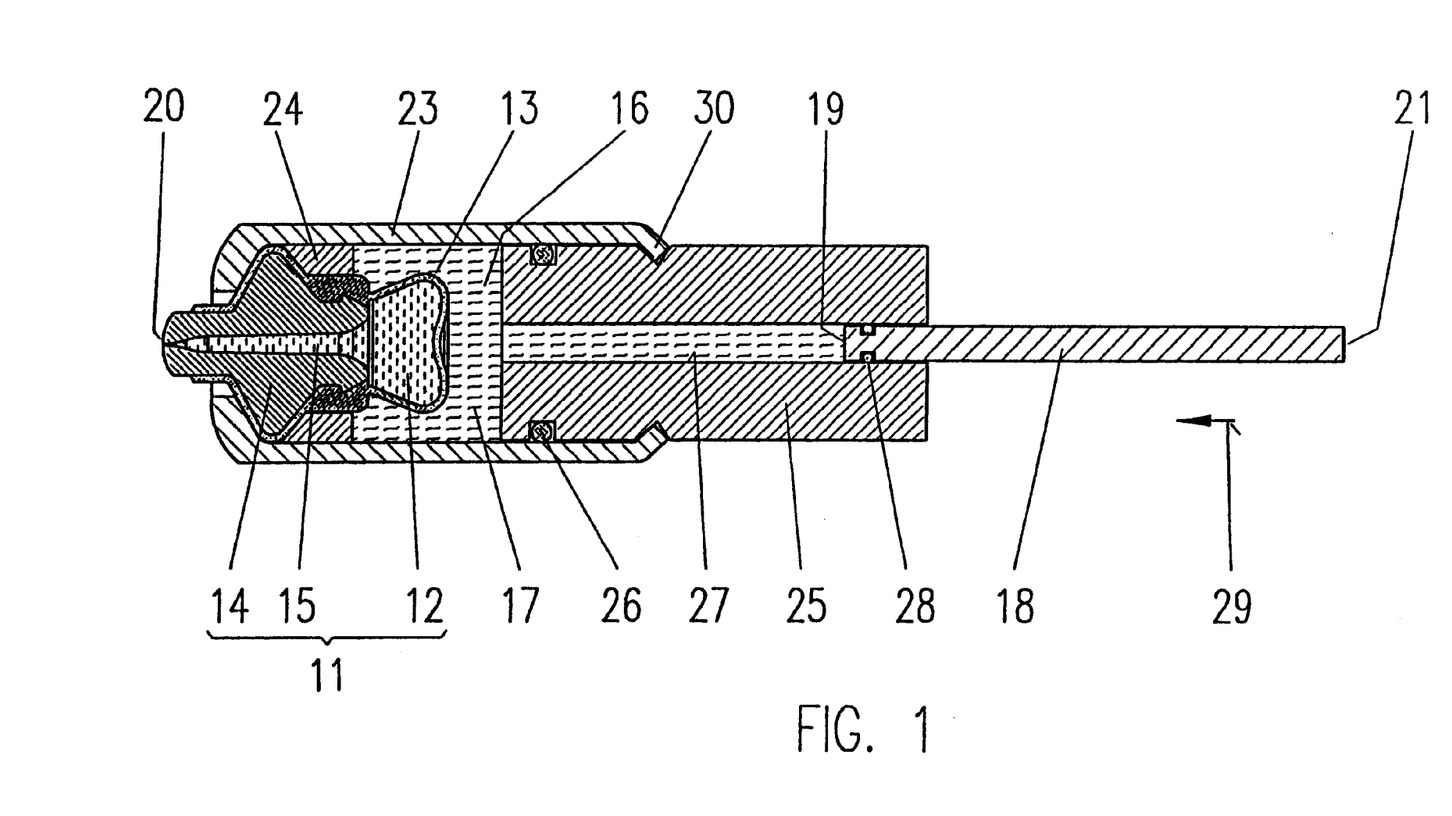
FIG. 1 shows a schematic cross sectional view of a basic structure of a needleless injection system according to the invention.

As can be appreciated from FIG. 1 a hypodermic needleless injection system according to the invention comprises in particular the following components: a medication unit 11, a hydrostatic chamber 16 and a piston 18. Not shown in FIG. 1 but equally part of the system depicted therein are an activatable force generator and activation means for activating the force generator.

Medication unit 11 is configured and dimensioned to store a volume of liquid 12 to be injected. Medication unit 11 has a first region comprising a medication container which has a thin, flexible wall 13 and a second region comprising an insert 14 having a jet nozzle 15. This nozzle 15 is in liquid communication with the medication container of the first region of medication unit 11. Wall 13 is deformable and collapsible. Jet nozzle 15 has an outlet 20 through which liquid 12 to be injected is ejected. Medication unit 11 is made of suitable construction materials, e.g. polyethylene and polypropylene, which are suitable for storing medications including sensitive protein drugs.

Hydrostatic chamber 16 contains a hydrostatic pressure transfer medium 17 and is so configured and dimensioned that medication unit 11 is located at least partially within the hydrostatic chamber 16 and that a pressure-exerted on transfer medium 17 would cause wall 13 of the first region of medication unit 11 to deform, so that the volume available for said liquid medication 12 in the first region is reduced. In a preferred embodiment wall 13 of the first region collapses under a pressure exerted thereon by transfer medium 17 and the entire volume of liquid medication 12 is ejected through jet nozzle 15.

In general terms hydrostatic pressure transfer medium 17 is a bio-compatible material which flows easily when subject to a pressure of about 200 to 300 bar and which is substantially incompressible. Transfer medium 17 transmits the piston pressure to the single dose medication container in a hydrostatic manner, is inert relative to the medication and other materials of construction, and is not expected to leak or evaporate over the storage life of the injection system.

Transfer medium 17 is preferably a gel, e.g. an elastomeric silicon gel. Such a gel is a very biocompatible material that is used e.g. in long-term human implants. In the unlikely event that particles of gel 17 would contact the liquid medication and thereby enter into a patients body, it is expected to be harmless. Transfer medium 17 can also be e.g. a soft rubber or a sterile saline solution.

Piston 18 has a first end 19 and a second end 21 opposite to first end 19. First end 19 has a surface which forms a closure of hydrostatic chamber 16, and is adapted for applying a pressure on gel 17 contained in hydrostatic chamber 16.

The injection system of FIG. 1 also comprises a metal housing 23 hermetically closed at one end by a bulkhead 25. Bulkhead 25 is held in this position against internal pressure forces in housing 23 by a crimp 30 or other equivalent secure fastening means. Bulkhead has a bore 27 partially filled with gel 17. Part of piston 18 is inserted in bore 27. A suitable piston seal element 28 ensures a sliding seal of bore 27 by piston 18. Medication container 11 is contained and positioned within housing 23 as shown by FIG. 1 so that it closes the other end of housing 23. Gel 17 fills hydrostatic chamber 16 which extends between the inner end of bulkhead 25 and medication container 11. A bulkhead seal 26 ensures hermetic closing of one end of hydrostatic chamber 16. A rubber element 24 holds medication container 11 in its position within housing 23 and hermetic closing of the opposite end of hydrostatic chamber 16.

When a force, such as the force represented by arrow 29 in FIG. 1, is applied to one end of piston 18 a corresponding pressure is applied by surface 19 of the opposite end of piston 18 on gel 17 in hydrostatic chamber 16 and gel 17 in turn applies that pressure hydrostatically on the deformable wall 13 of the first region of medication container, and this pressure causes ejection of the liquid contained in the latter container through nozzle 15. The size of surface 19 determines the pressure generated by a given force applied on piston 18, and the displacement of piston 18 in bore 27 determine the liquid volume displaced, i.e. the liquid volume injected. Therefore, in particular proper choice of these parameters (size of surface 19, stroke of piston 18) makes possible to achieve a required injection performance.

As described hereinafter in examples of specific embodiments a preferred embodiment of a needleless injection system according to the invention further comprises the following means not shown by FIG. 1:

an activatable force generator able to generate a force and to apply that force on the second end 21 of piston 18 in order to cause that the surface of the first end 19 of piston 18 applies a corresponding pressure on gel 17, and activation means for activating the force generator. A system having the structure shown in FIG. 1 has e.g. an jet nozzle 15 having a diameter of 0.2 millimeter. If the pressure applied on the flexible part of the medication container through gel 17 is e.g. 300 bar, the injection system provides an injection with a peak flow of 7 microliters per millisecond.

The detailed design of an injection system according to the invention is guided by the following experimental facts:

The diameter of orifice 20 of jet nozzle 15 influences the depth of penetration of the injected liquid. At a given pressure, a larger orifice diameter result in a deeper penetration. Subcutaneous injections jet orifice diameters are typically in the range from 0.10 to 0.25 millimeters diameter. In the following examples the diameter of orifice 20 of jet nozzle 15 is 0.2 millimeters.

The rate at which the pressure applied on the deformable medication container increases with time is critical in order to achieve a proper injection performance. A rapid initial rise to the peak injection pressure is necessary in order to achieve the required penetration depth. After initial penetration, a reduced pressure is required to deliver the medication without excessive penetration of the soft subcutaneous tissue. An initial pressure rise time to about 300 bar in less than a millisecond, followed by a 200 bar sustained pressure is typical for 200 microliter subcutaneous injection through a 0.2 millimeter diameter orifice of jet nozzle 15.

In general terms the above mentioned activatable force generator is so configured and dimensioned that it is adapted to provide the force to be applied to piston 18 with such a mechanical power that the corresponding pressure applied on transfer medium 17 rises to a peak value within a time interval which is equal to or shorter than about two milliseconds, and after that interval falls to a value which is lower than said peak value.

Different sources of stored energy including compressed springs or compressed gas can be used as force generator. In particular any one the following sources of stored energy can be used within the scope of the instant invention in order to provide e.g. a 50 millisecond power pulse with a peak value over 200 watts:

Pyrotechnic energy sources are ideal for delivering a short, high power pulse in a small space, and they have the advantage of providing the injection pressure directly, without need for pressure multiplication by means of a differential piston.

Liquid gas such as CO2 is a safe and effective energy source. Since the ambient temperature vapor pressure of CO2 is less than 60 bar, it is necessary to multiply this pressure by means of a differential area piston to reach the required 200 to 300 bar pressure for performing a proper injection. In principle any low-pressure source of pressurized gas or vapor may be utilized, e.g. acidi-carbonate reactions, low pressure stored nitrogen, fuel-air combustion, or low pressure pyrotechnics.

Pressurized gas at 300+ bar is an effective energy source that provides directly the required pressure level, provided that suitable storage vessels and release devices are available.

Rubber or plastic springs, in particular certain rubber or plastic springs store a large quantity of energy per unit mass compared to steel springs. The cost and performance of such rubber or plastic springs is attractive, provided that a long term stability of their properties and low load loss with time is ensured. Either factory cocked or user cocked rubber or plastic springs can be used.

Metal springs, in particular certain steel springs, store a large quantity of energy per unit mass. Either factory cocked or user cocked metal springs can be used.

Electrochemical gas generation obtained by dissociation of liquids such as water may be used to produce pressurized gas. The advantage of such a process is that a low power battery input over a period of time can generate a pressure that is adapted to be released rapidly released to provide the necessary pressure for performing the injection.

Electromechanical energy sources e.g. a DC motor powered by e.g. a Nickel-cadmium battery may be used to deliver the mechanical power pulse required for jet injection.

The choice of a suitable energy source for an injection system according to the invention depends on the particular application. An electromechanical power source may be suitable and very economical in a clinical setting where size is not an issue, while a spring or liquid gas energy source may be preferable for a single use disposable injection system.

In general terms an injection system according to the invention may be packaged and delivered to the user with or without power source depending from the intended use respectively the requirements/needs of the user.

The embodiment shown by FIG. 1 is an injection system without power source. Such a system is intended for use with a separate power module which can be e.g. a manually powered spring device or an automatic gas or electrically powered device.

Specific examples of particular embodiments of a needle-less injection system according to the invention including a power source are described hereinafter. Such systems are primarily single use disposable devices. Their integrated power source may be e.g. a spring or stored gas.

EXAMPLE 1

Figure 2:
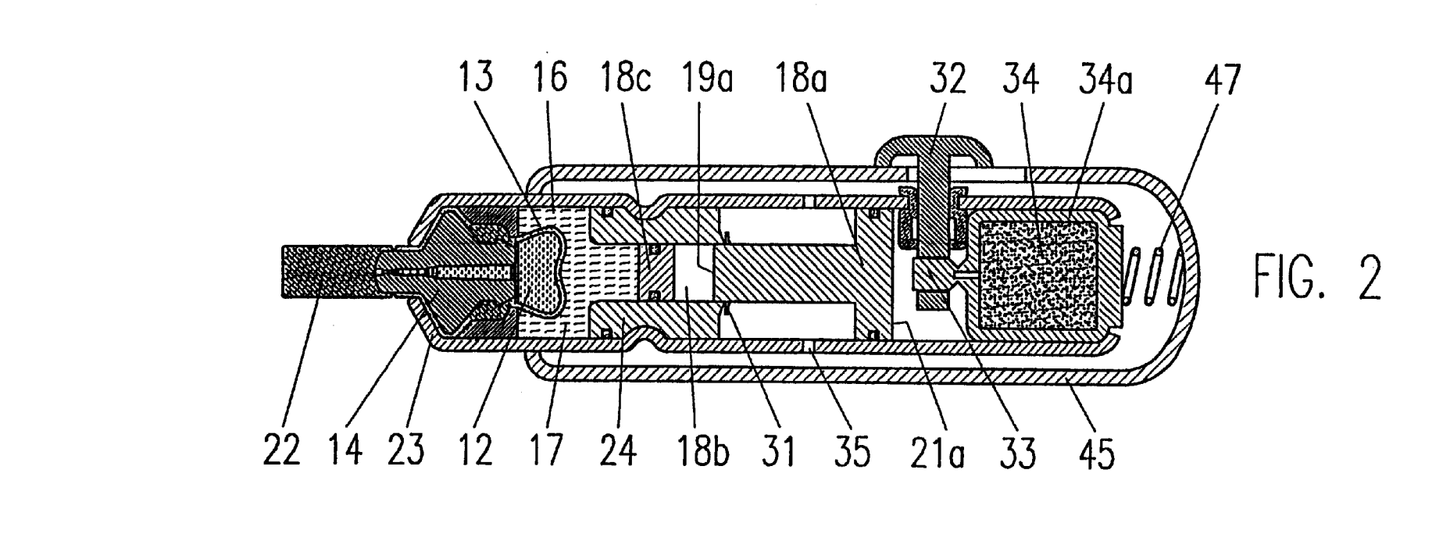
FIG. 2 shows a schematic cross sectional view of a first embodiment of a needleless injection system according to the invention before activation of the force generating means.
Figure 3:
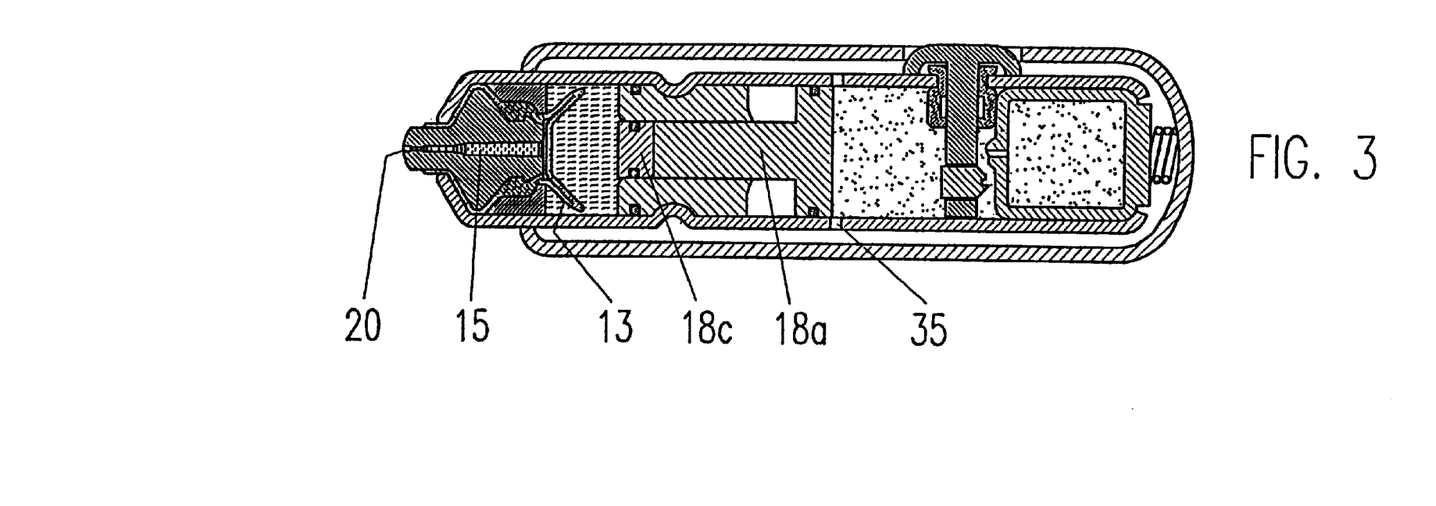
FIG. 3 shows a schematic cross sectional view of the embodiment shown by FIG. 2 after activation of the force generating means.

FIGS. 2 and 3 illustrate the structure and the operation of a first embodiment of a device according to the invention.

This first embodiment is essentially a disposable single use device comprising a force generator powered by a liquid-gas 34.

As shown by FIG. 2, in this embodiment liquid gas 34 contained in a reservoir 34a is used to generate the force to be exerted on a differential piston 18a. The means for generating such force further include a gas release valve 33 and a trigger 32 for actuating, that is for opening valve 33. These elements as well as a spring 47 are assembled and operatively connected to the other components of the system by a housing 45 which is adapted to slide over a housing 23 of the type described with reference to FIG. 1. Spring 47 serves for defining the level of mechanical pressure exerted by the system on the patient's skin that has to be attained in order to enable activation of the force generator by means of trigger 32. Gas release valve 33 is e.g. a breakable closure of an outlet of gas reservoir 34a, and in this case the latter closure is adapted to be broken by actuation of trigger 32.

Before use the different components of the injection system have the positions shown by FIG. 2, the outlet of jet nozzle 15 is closed by a tear-off closing tab 22, and trigger 32 is locked in place by a keyhole slot in sliding housing 45. This locking prevents accidental release of trigger 32.

Preparation of the injection system for performing an injection comprises the following steps:

removing closing tab 22 to open orifice 20, pressing the nose of the device on the skin of a patient causes housing 45 to slide over a portion of housing 23 and brings these housings to their positions shown by FIG. 3, this movement of housings 45 with respect to housing 23 compresses spring 47 and brings trigger 32 to a position where it can be pushed in order to open valve 33 and thereby let gas 34 escape and build up pressure on end surface 21 of differential piston 18a.

After the above described preparation steps, an injection can be performed by actuation of trigger 32.

When valve 33 is opened by actuation of trigger 32, the gas contained in reservoir 34a is released through valve 33, this gas evaporates and builds up pressure on end surface 21a of differential piston 18a. Piston 18a is restrained from motion by shear-off stop 31 until the pressure is high enough and exceeds a predetermined threshold value. When this happens shear-off stop 31 is cut and differential piston 18a is suddenly free to travel towards hydrostatic chamber 16 to impact on a plunger 18c and thereby to exert pressure on gel 17 contained in hydrostatic chamber 16. Remaining gas escapes through a vent hole 35.

Differential piston 18a makes possible to multiply the gas pressure applied on the surface of its end 21a, by a factor which is equal to the quotient of the surface of end 21a to the surface of end 19a of piston 18a. This factor is larger than one, because the surface of end 21 is larger the surface of end 19. In the embodiment shown by FIGS. 2 and 3, differential piston 18 steps up the pressure by a factor of about 6 to 1. Since the surface of end 19a of differential piston 18a impacts on a surface of same size of plunger 18c, the pressure exerted on hydrostatic gel 17 is equal to the gas pressure multiplied by the latter factor.

In the embodiment shown by FIGS. 2 and 3 the initial rise of the pressure exerted by gel 17 on deformable wall 13 is particularly high due to the impact pressure generated by the impact of piston 18a on plunger 18c. This impact pressure arises because of the existence of a predetermined separating space 18b, that is a free travel distance, between the initial position of end 19a of piston 18a and plunger 18c.

In the above described way a high hydrostatic pressure is generated which suddenly acts on gel 17. Gel 17 under pressure does in turn exert pressure on deformable wall 13 of medication unit 11. Thus the sudden gas release causes a fast rise of the hydrostatic gel pressure exerted on the deformable wall 13 and causes ejection of liquid medication 12 contained therein through jet nozzle 15 of insert 14 of the second region of medication unit 11.

FIG. 3 shows the configuration of the embodiment shown by FIG. 2 at the end of the injection.

Figure 6:
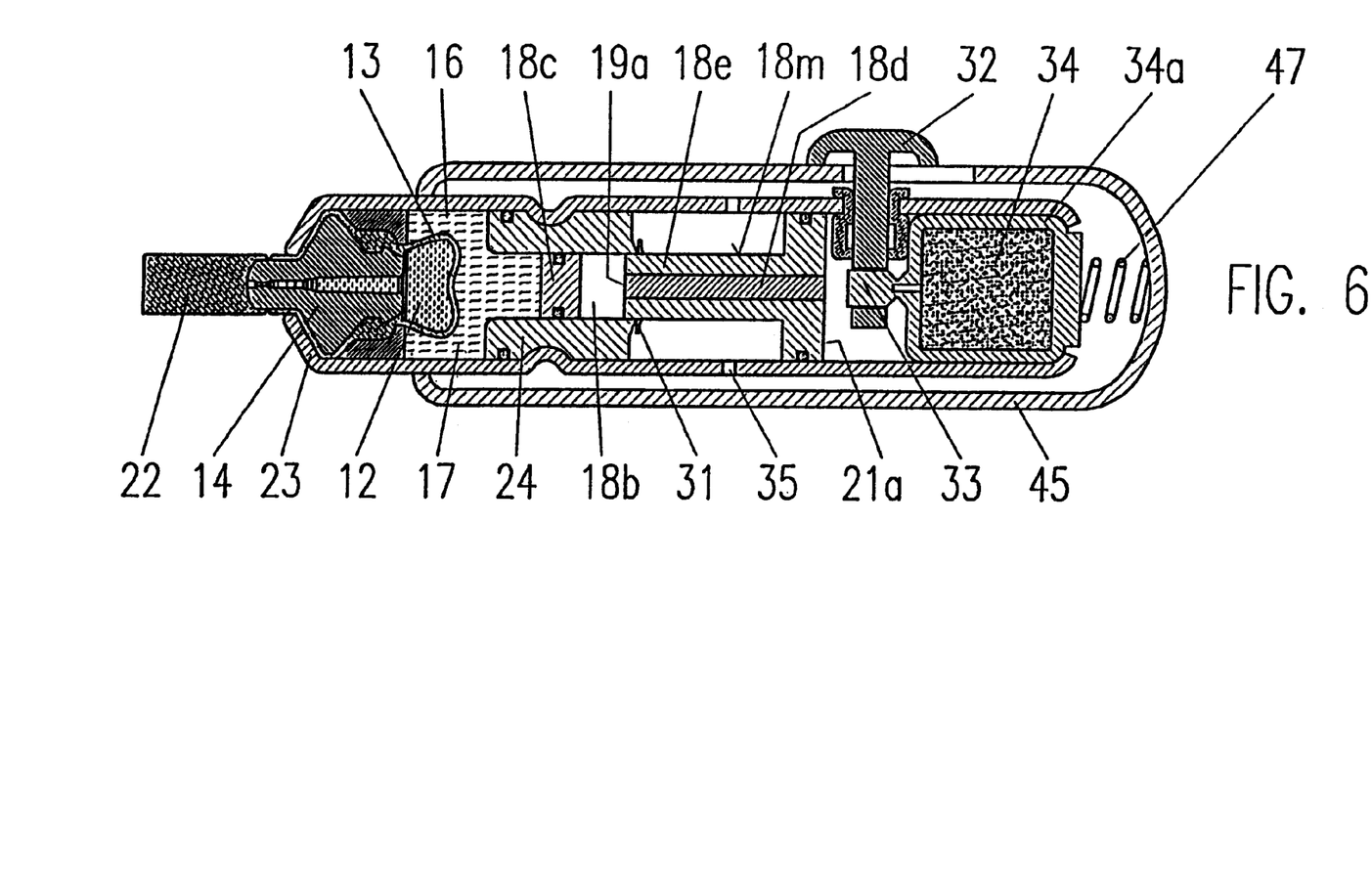
FIG. 6 shows a schematic cross sectional view of a variant of the first embodiment shown by FIG. 2.

FIG. 6 shows a schematic cross sectional view of a variant of the embodiment shown by FIG. 2. In the variant shown by FIG. 6, piston 18m comprises two parts: a first part 18d of a first material and a second part 18e of a second material, the second material having a higher density than the first material. First part 18d is e.g. a metallic core part, and second part 18e is e.g. a peripheral part made of a plastic material. The purpose of providing piston 18m with a heavier core part 18d is to increase the total mass of piston 18m in order to increase the force with which piston 18m impacts on plunger 18c, and thereby to shorten the rise time of the pressure pulse applied on gel 17 and therefore on collapsible wall 13 of medication unit 11.

EXAMPLE 2

Figure 4:
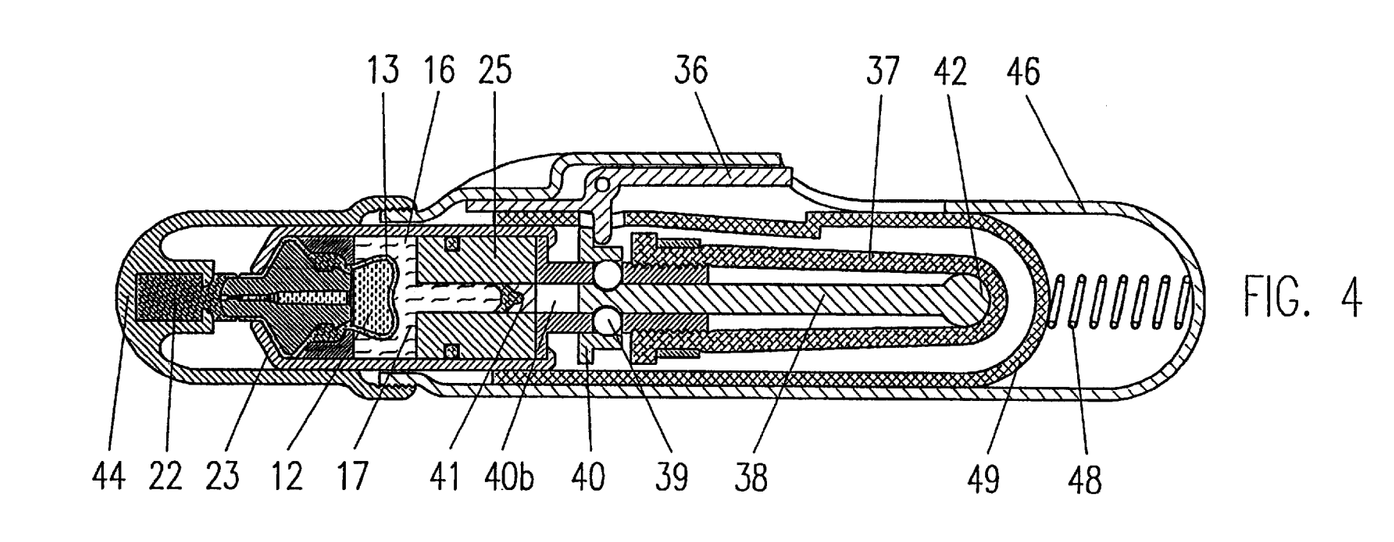
FIG. 4 shows a schematic cross sectional view of a second embodiment of a needleless injection system according to the invention before activation of the force generating means.
Figure 5:
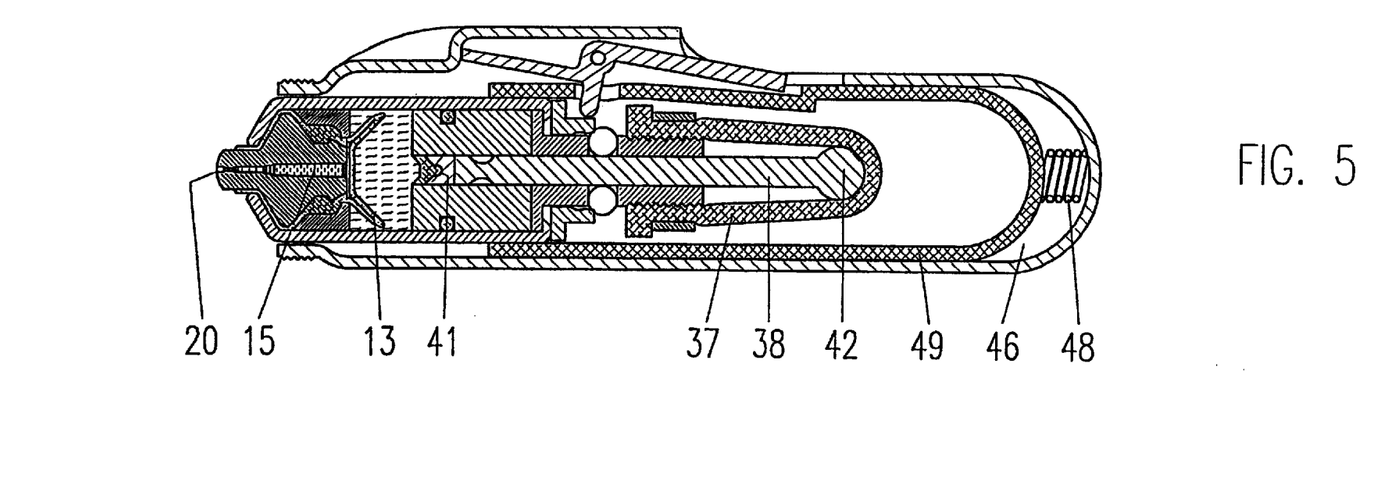
FIG. 5 shows a schematic cross sectional view of the embodiment shown by FIG. 4 after activation of the force generating means.

FIGS. 4 and 5 illustrate the structure and the operation of a second embodiment of a device according to the invention. This second embodiment is essentially a disposable single use device comprising a force generator powered by a rubber spring system.

As shown by FIG. 4, in this embodiment a molded rubber cup spring 37 is used to generate the force to be exerted on a push rod 38. When push rod 38 is displaced by a force generated by sudden relaxation of spring 37 a first end 40 of push rod 38 impacts on a piston 41 which then exerts a corresponding pressure on gel 17 contained in hydrostatic chamber 16. Push rod 38 and piston 41 thus perform a similar function as piston 18 in the embodiment described above with reference to FIGS. 2 and 3.

Spring 37 is factory preloaded to the cocked position shown by FIG. 4. In this position spring 37 exerts a force on a second end 42 of push rod 38. In a modified embodiment spring 37 is not preloaded at the factory and has to be brought by the user to the cocked position shown by FIG. 4.

The rubber chosen as material for the manufacture of rubber spring 37 must have the following properties: high strength, high elongation, and low loss of load over time. In a preferred embodiment cocked spring 37 is subject to thermal aging as a production step in order to ensure a stable performance over the storage life of the device.

A trigger 36 enables the user to effect a sudden relaxation of previously loaded spring 37. For this purpose trigger 36 comprises a ball latch 39 adapted for retaining and releasing push rod 38 depending from the position of trigger 36. Ball-latch 39 prevents displacement of push rod 38 as long as trigger 36 is in a first position shown in FIG. 4. Ball-latch 39 is so configured and dimensioned that it is unstable once it is triggered by bringing trigger 36 to the position shown in FIG. 5. This property of ball-latch 39 makes it suitable for suddenly releasing said push rod 38, for thereby allowing a sudden displacement of push rod 38 caused by a force generated by relaxation of rubber spring 37, and for thereby causing a fast rise of the pressure exerted by push rod 38 via piston 41 on gel 17, and a corresponding fast rise of the pressure exerted by gel 17 on deformable wall 13 of medication unit 11.

As shown by FIG. 4 the embodiment represented therein further comprises an inner housing 49 which is mechanically connected with pressure chamber housing 23 and an outer housing 46, which is adapted to slide over inner housing 49, and a spring 48 located between inner housing 49 and outer housing 46, which spring 48 serves for defining the level of mechanical pressure exerted by the system on the patient's skin that has to be attained in order to enable activation of the force generator by means of trigger 36.

Before use the different components of the injection system have the positions shown by FIG. 4 and the outlet of jet nozzle 15 is closed by a tear-off closing tab 22 and protected by a removable cap 44 which facilitates removal of closing tab 22. Removable cap 44 also serves for locking outer housing 46 in position with respect to inner housing 49 and thereby prevents accidental release of trigger 36.

Preparation of the injection system for performing an injection comprises the following steps:

removing cap 44 and closing tab 22 to open orifice 20, pressing the nose of the device on the skin of a patient causes outer housing 46 to slide over a portion of inner housing 49 and brings these housings to their positions shown by FIG. 5, this movement of housing 46 with respect to housing 49 compresses spring 48 and brings trigger 36 to a position where it can be pushed in order to release ball-latch 39 and thereby suddenly release push rod 38.

After the above described preparation steps, an injection can be performed by actuation of trigger 36.

When trigger 36 is actuated after the preparation steps just described, ball latch 39 suddenly releases push rod 38 and thereby allows sudden relaxation of rubber spring 37. This relaxation causes push rod 38 to impact on piston 41 which in turn suddenly exerts an hydrostatic gel pressure on the deformable wall 13 and causes ejection of liquid medication 12 contained therein through jet nozzle 15 of insert 14 of the second region of medication unit 11.

In the embodiment shown by FIGS. 4 and 5 the initial rise of the pressure exerted by gel 17 on deformable wall 13 is particularly high due to the impact pressure generated by the impact of push rod 38 on piston 41. This impact pressure arises because of the existence of a predetermined separating space 40b, that is a free travel distance, between the initial position of end 40 of push rod 38 and piston 41.

FIG. 5 shows the configuration of the embodiment shown by FIG. 4 at the end of the injection.

Figure 7:
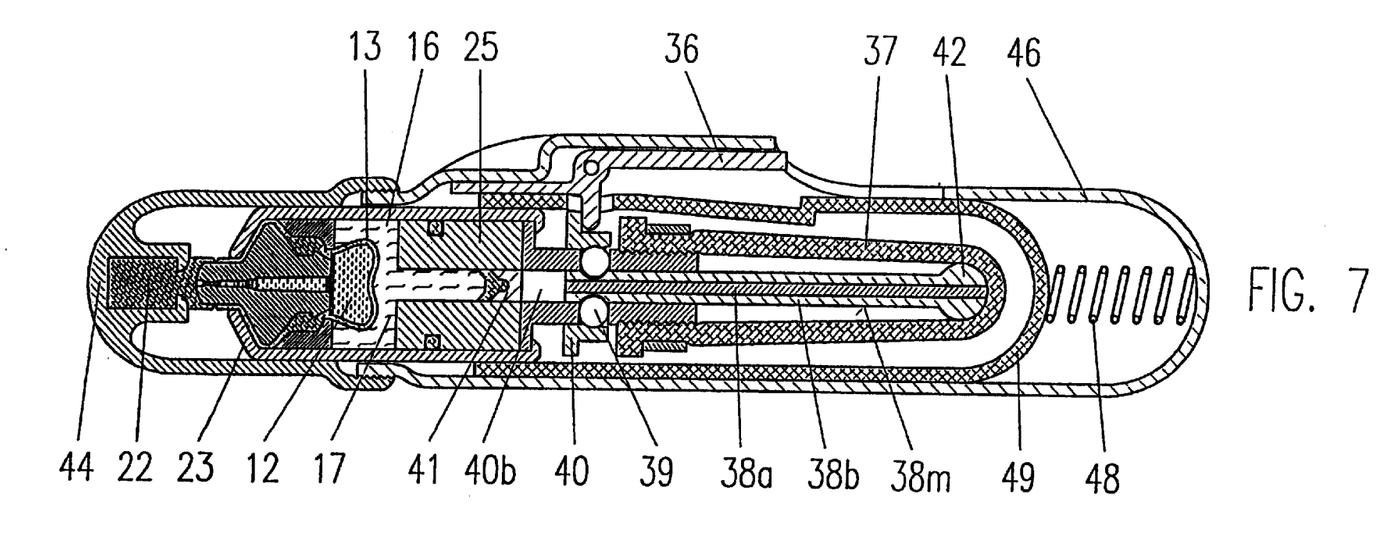
FIG. 7 shows a schematic cross sectional view of a variant of the first embodiment shown by FIG. 4.

FIG. 7 shows a schematic cross sectional view of a variant of the first embodiment shown by FIG. 4.

In the variant shown by FIG. 7, push rod 38m comprises two parts: a first part 38a of a first material and a second part 38b of a second material, the second material having a higher density than the first material. First part 38a is e.g. a metallic core part, and second part 38b is e.g. a peripheral part made of a plastic material. The purpose of providing push rod 38m with a heavier core part 38a is to increase the total mass of push rod 38m in order to increase the force with which push rod 38m impacts on piston 41, and thereby to shorten the rise time of the pressure pulse applied on gel 17 and therefore on collapsible wall 13 of medication unit 11.

LIST OF REFERENCE NUMBERS 11 medication unit
12 liquid medication
13 deformable wall of first region of medication container
14 insert of second region of medication container
15 jet nozzle
16 hydrostatic chamber
17 gel
18 first piston
18a second piston (differential piston)
18b separating space
18c plunger
18d core part of first piston 18m
18e peripheral part of first piston 18m 18m second piston (differential piston)
19 first end of first piston 18
19a first end of second piston 18a
20 orifice
21 second end of first piston 18
21a second end of second piston 18a
22 tear-off closing tab
23 housing of pressure chamber
24 rubber seal
25 bulkhead
26 bulkhead seal
27 cylindrical bore
28 piston seal
29 force
30 assembly crimp
31 shear-off stop
32 trigger
33 gas release valve
34 liquid gas reservoir
35 vent hole
36 trigger
37 rubber cup spring
38 push rod
38a core part of push rod 38m
38b peripheral part of push rod 38m
38m push rod
39 ball-latch
40 first end of push rod
40b separating space
41 piston
42 second end of push rod 38
44 cap
45 outer housing
46 outer housing
47 spring
48 spring
49 inner housing Although a preferred embodiment of the invention has been described using specific terms, such description is for illustrative purposes only, and it is to be understood that changes and variations may be made without departing from the spirit or scope of the following claims.

What is claimed is:

1. A hypodermic needleless injection system for injecting a liquid medication, which system comprises:
   (a) a medication unit configured and dimensioned to store a volume of liquid to be injected, said medication unit having a first region and a second region that are in liquid communication with each other, said first region being deformable and said second region having at least one orifice,
   (b) a hydrostatic chamber containing a hydrostatic pressure transfer medium, said hydrostatic chamber being so configured and dimensioned that the medication unit is located at least partially within the hydrostatic chamber and so that a pressure exerted on said transfer medium would cause said first region of said medication unit to deform so as to reduce the volume available for said liquid medication within said medication unit, and
   (c) a first piston having a first end and a second end opposite to said first end, said first end having a surface which is adapted for applying a pressure on said transfer medium contained in said hydrostatic chamber.

2. An hypodermic injection system according to claim 1 which further comprises
   (d) an activatable force generator able to generate a force and to apply said force on said second end of said first piston in order to cause that said surface of said first end of said first piston applies a corresponding pressure on said transfer medium, and
   (e) and activation means for activating said force generator.

3. An hypodermic injection system according to claim 2, wherein said activatable force generator is so configured and dimensioned that it is adapted to provide said force with such a mechanical power that said pressure applied on said transfer medium rises to a peak value within a time interval which is equal to or shorter than about two milliseconds, and after that interval falls to a value which is lower than said peak value.

4. An hypodermic injection system according to claim 2, wherein said activatable force generator comprises a container (34a) of a liquid gas.

5. An hypodermic injection system according to claim 2, wherein said activatable force generator comprises a spring as force generating element.

6. An hypodermic injection system according to claim 4, which further comprises
   a second piston which is adapted to exert a force on said first piston, and
   a shear-off member which prevents that said force generated by said force generator causes a displacement of said second piston as long as said force does not exceed a predetermined threshold value, said shear-off member being so configured and dimensioned that it breaks when said force reaches said predetermined threshold value and thereby allows a sudden displacement of said second piston (18a) caused by said force generated by said force generator.

7. An hypodermic injection system according to claim 6, wherein said second piston has a first part of a first material and a second part of a second material, said second material having a higher density than said first material.

8. An hypodermic injection system according to claim 5, which further comprises a push rod which is adapted to exert a force on said first piston, and wherein said activation means for activating said force generator comprise a ball-latch for preventing displacement of said push rod as long as said force generator is not activated by said activation means, said ball-latch being so configured and dimensioned that it is unstable once it is triggered and is thereby adapted for suddenly releasing said push rod and thereby allowing a sudden displacement of said of said push rod caused by said force generated by said force generator.

9. An hypodermic injection system according to claim 8, wherein said push rod has a first part of a first material and a second part of a second material, said second material having a higher density than said first material.

10. An hypodermic injection system according to claim 1, wherein said d hydrostatic pressure transfer medium is a bio-compatible material which flows easily when subject to a pressure of about 300 bar and which is substantially incompressible.

11. An hypodermic injection system according to claim 1, wherein said hydrostatic pressure transfer medium is a gel.

12. An hypodermic injection system according to claim 11, wherein said gel is an elastomeric silicon gel.

13. An hypodermic injection system according to claim 1, herein said hydrostatic pressure transfer medium is a soft rubber.

14. An hypodermic injection system according to claim 1, wherein said hydrostatic pressure transfer medium is a sterile saline solution.

* * * * *

UNITED STATES PATENT AND TRADEMARK OFFICE
CERTIFICATE OF CORRECTION

PATENT NO. : 6,440,099 B2  Page 1 of 1
DATED : August 27, 2002
INVENTOR(S) : Haar et al.

It is certified that error appears in the above-identified patent and that said Letters Patent is hereby corrected as shown below:

Column 8,
Line 66, delete "first" and insert -- second --.
Line 67, delete "first" and insert -- second --.

Column 9,
Line 18, delete "reservoir".
Line 19, insert -- 34a    gas reservoir --.

Signed and Sealed this

Twenty-eighth Day of January, 2003

JAMES E. ROGAN
*Director of the United States Patent and Trademark Office*